United States Patent [19]

Bar-Shalom

[11] Patent Number: 5,143,718

[45] Date of Patent: Sep. 1, 1992

[54] ANTIPERSPIRANT COMPOSITION

[75] Inventor: Daniel Bar-Shalom, Kokkedal, Denmark

[73] Assignee: Riemann Trading ApS, Naerum, Denmark

[21] Appl. No.: 487,967

[22] PCT Filed: Sep. 6, 1988

[86] PCT No.: PCT/DK88/00148

§ 371 Date: May 14, 1990

§ 102(e) Date: May 14, 1990

[87] PCT Pub. No.: WO89/02264

PCT Pub. Date: Mar. 23, 1989

[30] Foreign Application Priority Data

Sep. 15, 1987 [DK] Denmark .................. 4835/87

[51] Int. Cl.$^5$ .................... A61K 7/32; A61K 7/38
[52] U.S. Cl. ........................ 424/47; 424/65; 424/68
[58] Field of Search ............ 424/401, 47, 69, 664, 424/685, 68, 65; 514/828, 901, 858

[56] References Cited

U.S. PATENT DOCUMENTS

| 2,087,161 | 1/1937 | Moore | 167/90 |
|---|---|---|---|
| 3,608,086 | 9/1971 | Halpern | 514/557 |
| 3,856,941 | 12/1974 | Turner | 514/492 |
| 4,205,062 | 5/1980 | Däahn | 424/65 |
| 4,226,850 | 10/1980 | Packman | 424/47 |
| 4,369,173 | 1/1983 | Causland | 424/47 |
| 4,411,883 | 10/1983 | Kenkare | 424/47 |
| 4,774,079 | 9/1988 | Shin | 424/69 |
| 4,806,338 | 2/1989 | Smith | 424/47 |
| 4,832,945 | 5/1989 | Osipow | 424/65 |

FOREIGN PATENT DOCUMENTS

| 0070517 | 1/1983 | European Pat. Off. . |
|---|---|---|
| 2211188 | 10/1972 | Fed. Rep. of Germany . |
| 2423637 | 11/1975 | Fed. Rep. of Germany . |
| 118543 | 4/1947 | Sweden . |
| 365115 | 3/1974 | Sweden . |

OTHER PUBLICATIONS

Remington's Pharmaceutical Sciences Treatise, Mack Publishing Co., 17th Ed., 1985, pp. 777-778.

Holze et al., "Mechanism of Antiperspirant Action of Aluminum Salts", *J. Soc. Cosmet. Chem* 30, 279-295 (Sep./Oct., 1979).

Shelley et al., "Studies on Topical Antiperspirant Control of Axillary Hyperhidrosis" *Acta Dermatonvener* (Stockholm) 55: 241-260, 1975.

*Primary Examiner*—Thurman K. Page
*Assistant Examiner*—D. Colucci
*Attorney, Agent, or Firm*—Foley & Lardner

[57] ABSTRACT

An antiperspirant composition comprising $AlCl_3$ and an aluminum salt of at least one organic acid dissolved or dispersed in a suitable carrier, said acid being present in an amount capable of substantially neutralizing the amount of hydrogen chloride formed by the hydrolysis of the amount of $AlCl_3$ present, said $AlCl_3$ and said aluminium salt or salts of the acid or acids being present in said composition in amounts corresponding to a total aluminium content of up to 3.0 gram atom per kilogram of composition.

10 Claims, No Drawings

ANTIPERSPIRANT COMPOSITION

FIELD OF THE INVENTION

The present invention relates to an antiperspirant composition as well as a method for controlling perspiration without the disadvantages often associated with such methods.

BACKGROUND OF THE INVENTION

It is a well known fact that $AlCl_3$ is a most effective antiperspirant salt (Holtze E., Kligman A.: "Mechanism of antiperspirant aluminium salts." *J. Soc. Cosmet. Chem.* 30, 279 (1979), and Shelley B., Hurley H.J.: "Studies on topical antiperspirant control of axillary hyperhydrosis." *Acta Dermatoven. Stockh.* 55, 241 (1975)). Most of the comercially available antiperspirant compositions contain $AlCl_3$ as the active component, e.g. dissolved in a suitable solvent. $AlCl_3$ exerts its antiperspirant activity by reacting with water to form aluminium hydroxychloride which acts as an astringent and thereby reduces the sweat output of the sweat glands. However, the disadvantage of using $AlCl_3$ is that the reaction with water to form aluminium hydroxychloride also generates hydrogen chloride or hydrochloric acid as a side product which may cause local skin irritation because of the high acidity; in most clinical studies, 20–50% of the members of the test groups indicated that irritation occurred, and about 10% reported severe irritation (soreness). Also, clothes in contact with the application area may be damaged, and both of these adverse effects can be ascribed to the formation of hydrochloric acid on the skin and in the sweat ducts.

Also, the antiperspirant activity of $AlCl_3$ is furthermore believed to be partly due to the aluminium hydroxychloride forming a perspiration-blocking "cast" of a polymeric gel precipitate in the sweat ducts. However, the acidity generated in sweat which reacts with $AlCl_3$ will impair the efficiency of the $AlCl_3$-containing composition since $AlCl_3$ is not capable of forming the gel precipitate when the water with which it reacts has a pH of less than 5; among other things this means that the $AlCl_3$ composition is not effective when used during sweating.

In the known art, several attempts have been made to prevent the development of acid which causes skin irritation and damaging of clothes. Thus, European Patent No. 70517 describes a two-part kit comprising an $AlCl_3$-containing composition and a basic buffer composition, the basic composition being applied subsequent to the $AlCl_3$-containing composition but after having allowed the $AlCl_3$-containing composition to work for a certain specified period of time. However, as will be self-evident, such a two-stage application sequence is not very practical in actual use since most users would much prefer to have the antiperspirant treatment conducted in a single application.

From the above it is clear that there is a need for an antiperspirant composition which, while still having the advantages conferred by $AlCl_3$, does not have the consequent disadvantages and which at the same time is simple to use.

SUMMARY OF THE INVENTION

The above described disadvantages in the known art are avoided in the antiperspirant composition of the invention which comprises $AlCl_3$ and one or more aluminium salts of one or more acids dissolved and/or dispersed in a suitable carrier, the acid or acids having no pK value in aqueous solution lower than 2.5 and being present in an amount capable of substantially neutralising the amount of hydrogen chloride formed by the hydrolysis of the amount of $AlCl_3$ present.

The idea behind the invention is to exploit the high acidity of hydrogen chloride by allowing the hydrogen chloride to react with a salt of the weaker acid with no pK value below 2.5, the weaker acid then, according to well known principles, being liberated from the salt by the stronger hydrochloric acid to give the free weaker acid and a chloride instead. The fact that an aluminium salt of the weaker acid is used has the advantage of resulting in the formation of a further amount of aluminium hydroxychloride, thereby resulting in a further antiperspirant effect. On the other hand, the acidity is lowered considerably since the free acid present in the skin environment is now not solely hydrogen chloride but is in effect the weaker acid with no pK value below 2.5, the aluminium salt of which forms part of the composition of the invention. Since a weaker acid is less irritant to the skin, the net result is a reduction in or elimination of the skin irritation.

DETAILED DESCRIPTION OF THE INVENTION

In order to prevent premature reaction of the aluminium chloride with water, it is preferred that the composition is anhydrous. This is in particular obtained by using a carrier system which is anhydrous or has no available water so that aluminium chloride does not undergo hydrolysis to aluminium hydroxychloride and hydrogen chloride. The term "no available water" is intended to mean that the water present in the formulation is not able to solvate the aluminium salts, either because the water is present in too small an amount, or because the water is bound too strongly by another component in the composition. Thus, $AlCl_3$ will for example not undergo hydrolysis in 95% ethanol or in liquid sorbitol.

A preferred composition is one in which the weaker acid/acids has/have no pK value below 3, in particular not below 3.5, especially not below 4. The use of an acid or acids with such properties will ensure a significant reduction in the level of skin irritation. The acid or acids is/are preferably physiologically acceptable.

Since a number of organic acids have various biological properties, it is preferred that an acid in the composition of the invention has a biological effect such as astringent, antibacterial, antimicrobial, antiseptic, antifungal, antiparasitic, antiperspirant, deodorant, antiinflammatoric, emollient, anesthetic, hemostatic, antipruritic properties, etc. By using an aluminium salt of one or more acids with one or more such properties, the properties of the composition of the invention may be amplified as well as expanded in its spectrum. Thus, if the acid used in the composition of the invention has antifungal properties, the composition of the invention could be useful in therapy or profylactic treatment of *Tinea pedis*, also known as "athlete's foot". This affliction is extremely common and is associated with sweating, and the maceration of the skin by the sweat facilitates the infection and makes it more difficult to treat. Even in persons with "normal" sweating it is desirable to reduce the amount of perspiration when treating the fungi.

Potentially useful acids with no pK value in aqueous solutions below 2.5 are the following: acetic, propionic, citric, acetylsalicylic, benzoic, salicylic, ascorbic, nicotinic, tartaric, phtalic, lactic, fatty acids (oleic, linoleic, undecenoic, octanoic, palmitic, ricinoleic, stearic, etc.), acetylcretosinic, succinic, carbamoylphenoxyacetic, diacetylsalicylic, anthranilic, mefenamic, gentisic, tolfenamic, acetotartaric, agaric, formic, subacetic, ellagic, fumaric, malic, morrhuic, oxalic, para-amino-benzoic, gallic, cinnamic, isoascorbic, sorbic, aminocaproic, aminomethylbenzoic, tranxenamic acid, naturally occuring amino acids such as glycine, alanine, valine, leucine, isoleucine, serine or threonine, etc, and derivatives thereof as well as tar acids, phenol, thymol and cation exchange resins. The term "derivatives thereof" is intended to mean that the various acids listed may also be further substituted with various groups, the presence of derivative substituents conferring one or more of the biological properties mentioned above to the acid in question. The substituent groups forming the derivatives may be selected from a broad range such as phenyl, phenylamino, naphtyl, benzoyl, indenyl or various heterocyclic groups such as indolyl, benzoxazolyl, pyridyl, benzindolyl etc., the substituent groups optionally themselves being substituted with substituents such as halogen, alkyl, alkoxy, optionally alkylsubstituted amino etc.

Thus, various derivatives of propionic, acetic, phenylacetic, salicylic, and anthranilic acid etc. are able to inhibit prostaglandin synthesis and can therefore function as local antiinflammatoric agents. Examples of propionic acid derivatives are naproxen, ibuprofen, benoxaprofen, and bucloxic acid; examples of phenylacetic and acetic acid derivatives are indomethacin, bufexamac, diclofenac, sulindac, and aclofenac; examples of salicylic acid derivatives are aspirin, acetaminosalol, diflunisal, dipyrocetyl, and fendosal; examples of anthranilic acid are etofenamic acid, flufenamic acid, meclofenamic acid, and tolfenamic acid; and an example of butyric acid derivatives is fenbufen.

Among the acids listed above, several are known to have some of the biological properties mentioned above. Thus, salicylic, acetotartaric, agaric, formic, subacetic and ellagic acid are known to have astringent properties, and undecenoic, octanoic, propionic, tolfenamic, isoascorbic and sorbic acid are known to have antifungal properties.

Preferred examples of acids having no pK value below 2.5 are acetylsalicylic, salicylic, benzoic, propionic, octanoic, undecanoic, sorbic acid, ascorbic acid, lactic acid, malic acid, stearic acid, citric acid, phthalic acid, tartaric acid, or a naturally occurring amino acid.

In order to ensure satisfactory neutralization of any hydrogen chloride liberated as a result of the reaction between $AlCl_3$ and water, the molar ratio between the aluminium salt or salts of the acid or acids and $AlCl_3$ is preferably in the range from 1:1 to 1:2, in particular about 2:3.

In order to provide a composition effective for antiperspirant purposes, it is preferred that the $AlCl_3$ and the aluminium salt of the acid is present in the composition of the invention in amounts corresponding to a total aluminium content of up to 3 gram atoms of Al per kilogram of composition, in particular from 1.0 to 2.0 gram atoms Al per kg composition.

The carrier or carriers in which the $AlCl_3$ and the aluminium salt of the weaker acid is dissolved and/or dispersed may be any of the carriers traditionally used for incorporation into antiperspirant compositions. Thus, the carrier may be a liquid, a gel, a semisolid or a powder. Liquid carriers may be alcohols, glycols, fats, fatty acid esters, fatty acids, paraffins, liquid polymers (such as silicone oil), for example ethyl alcohol, isopropyl myristate, glycerine, propylene glycol, etc. as well as mixtures thereof. A gel carrier may be an alcohol or another of the above mentioned liquid carriers such as ethyl alcohol containing a cellulose derivative such as hydroxypropyl cellulose. A semisolid carrier may be a polyglycol, a paraffin (for example vaseline), fats, or any of the above mentioned liquids containing a polymer such as liquid paraffin containing dissolved polyethylene (marketed under the trade name Plastibase). A solid carrier may be talc, starch, kaolin etc.

The invention further relates to a method for controlling perspiration comprising applying to a skin area where perspiration is to be controlled an antiperspirant composition as described above.

The composition of the invention may be prepared by methods commonly used within the art for the preparation of antiperspirant compositions, the preparation ordinarily comprising simply mixing together the constituents. Thus, a liquid composition may be prepared by dissolving or dispersing the aluminium chloride and the weaker acid/acids in the liquid carrier; optionally, the aluminium chloride and the weaker acid/acids may be dissolved or dispersed separately in two portions of the carrier or in two different carrier components followed by mixing of the mixtures. A gel composition may be obtained by starting from a liquid composition and adding gelling agent such as the above mentioned cellulose derivative.

The invention is further illustrated by the following non-limiting examples.

EXAMPLE 1

An antiperspirant composition was prepared from the following ingredients:

| | |
|---|---|
| Aluminium chloride | 10.0 g |
| Aluminium hydroxydisalicylate | 12.5 g |
| Isopropyl myristate | 10.0 ml |
| Absolute ethanol q.s. | 100.0 ml |

The aluminium chloride was dissolved in about 50 ml absolute ethanol to form a solution. The aluminium hydroxydisalicylate was dispersed thoroughly in the isopropyl myristate, and to the resulting dispersion, the aluminium chloride solution was added while stirring to give an antiperspirant composition comprising a dispersion of aluminium hydroxydisalicylate in a liquid medium comprising aluminium chloride, isopropyl myristate, and absolute ethanol.

TEST

The composition prepared above (composition II) was tested by comparison with a classical type antiperspirant consisting of a 20% w/w solution of aluminium chloride in absolute ethanol (composition I). Ten volunteers applied composition I to their left armpit and composition II to their right armpit for 10 days. Thereafter, the application pattern was switched around so that composition I was applied to the right armpit and composition II to the left, the application again being continued for 10 days. Eight out of the ten persons reported some kind of irritation in the armpit to which composition I was applied, whereas only one person on two of the total of twenty test days reported some irritation in the armpit when using composition II. The antiperspirant effects of the two compositions were the same.

EXAMPLE 2

Other compositions according to the invention comprise:

| A: | Aluminium chloride | 10.0 g |
|---|---|---|
| | Aluminium hydroxydibenzoate | 10.0 g |
| | Aluminium hydroxydisalicylate | 5.0 g |
| | Isopropyl myristate | 8.0 ml |
| | Absolute ethanol q.s. | 100.0 ml |
| B: | Aluminium chloride | 10.0 g |
| | Aluminium hydroxydibenzoate | 8.0 g |
| | Aluminium hydroxydisalicylate | 4.0 g |
| | Aluminium hydroxydiundecanoate | 3.0 g |
| | Excipient q.s. | 100.0 g |

The excipient in composition B may be e.g. talc giving a solid composition.

EXAMPLE 3

Antiperspirant Ointment

An antiperspirant ointment was prepared from the following ingredients:

| Polyethylen glycol 3000 | 175.0 g |
|---|---|
| Polyethylen glycol 400 | 175.0 g |
| 25% solution of AlCl$_3$ in absolute ethanol | 750.0 g |
| Aluminium hydroxydilactate | 120.0 g |
| Absolute ethanol | 160.0 g |

The polyethylen glycols were mixed in a melt whereupon the remaining ingredients were mixed into the melt in a high-shear homogenizer resulting in an ointment upon cooling.

EXAMPLE 4

Antiperspirant Stick

An antiperspirant stick was prepared from the following ingredients:

| Aluminium tristearate | 11.0 g |
|---|---|
| Polyethylene glycol 6000 | 10.0 g |
| Stearyl alcohol | 10.0 g |
| Polyethylene glycol 400 monostearate | 10.0 g |
| Aerosil (very fine silica) | 2.0 g |
| 25% solution of AlCl$_3$ in absolute ethanol | 40.0 g |
| Aluminium hydroxydilactate | 10.0 g |
| Absolute ethanol q.s. | to 100.0 g |

Aluminium stearate, polyethylene, glycol 6000, stearyl alcohol and polyethylene glycol 400 monostearate were mixed by melting the ingredients together. Thereafter, aerosil, ethanol and AlCl$_3$-solution in ethanol was added and mixed followed by addition and mixing of aluminium hydroxydilactate. Finally, the mixture was cooled in a mould giving an antiperspirant stick.

I claim:

1. An antiperspirant composition comprising AlCl$_3$ and an aluminium salt of at least one organic acid dissolved or dispersed in a suitable carrier, said acid, being selected from the group consisting of acetic, propionic, citric, acetylsalicylic, benzoic, salicylic, ascorbic, nicotinic, tartaric, phtalic, lactic, oleic, linoleic, undecenoic, octanoic, palmitic, ricinoleic, stearic, acetylcretosinic, succinic, carbamoylphenoxyacetic, diacetylsalicylic, anthranilic, mefenamic, gentisic, tolfenamic, acetotartaric, agaric, formic, subacetic, ellagic, fumaric, malic, morrhuic, oxalic, para-amino-benzoic, gallic, cinnamic, isoascorbic, sorbic, aminocaproic, aminomethylbenzoic, tranxenamic, glycine, alanine, valine, leucine, isoleucine, serine and threonine and being present in an amount capable of substantially neutralising the amount of hydrogen chloride formed by the hydrolysis of the amount of AlCl$_3$ present, said AlCl$_3$ and said aluminium salt or salts of the acid or acids being present in said composition in amounts corresponding to a total aluminium content of up to 3.0 gram atom per kilogram of composition.

2. An antiperspirant composition as claimed in claim 1 in which the carrier is anhydrous or has no available water for the hydrolysis of AlCl$_3$.

3. A composition as claimed in claim 1 which the acid or acids has/have antiperspirant, deodorant, astringent, antiseptic, antimicrobial, antifungal, or antiinflammatoric properties.

4. A composition as claimed in claim 1 in which said organic acid is selected from the group consisting of acetylsalicylic acid, salicylic acid, benzoic acid, propionic acid, octanoic acid, undecanoic acid, sorbic acid, ascorbic acid, lactic acid, malic acid, citric acid, phthalic acid, tartaric acid, glycine, alanine, valine, leucine, isoleucine, serine and threonine.

5. A composition as claimed in claim 1 in which the molar ratio between the aluminum salt of salts of the acid or acids and AlCl$_3$ is in the range from 1:1 to 1:2.

6. A composition as claimed in claim 5 in which the molar ratio between the aluminium salt or salts of the acid or acids and AlCl$_3$ is about 2:3.

7. A composition as claimed in claim 1 in which the AlCl$_3$ and the aluminium salt or salts of the acid or acids is present in the composition in amounts corresponding to a total aluminium content of from 1.0 to 2.0 gram atoms Al per kg composition.

8. A composition as claimed in claim 1 in which the carrier is a liquid, a gel, a semisolid, or a powder.

9. A method for controlling perspiration, comprising applying, to a skin area where perspiration is to be controlled, an antiperspirant composition according to claim 1.

10. A cosmetic method for controlling perspiration, comprising applying, to a skin area where perspiration is to be controlled, an antiperspirant composition according to claim 1.

* * * * *